(12) United States Patent
Ochiai et al.

(10) Patent No.: US 12,133,942 B2
(45) Date of Patent: Nov. 5, 2024

(54) MANUAL BREAST PUMP

(71) Applicant: PIGEON CORPORATION, Tokyo (JP)

(72) Inventors: Yukifumi Ochiai, Tokyo (JP); Katsutoshi Takahashi, Tokyo (JP); Tatsuyuki Ishikawa, Tokyo (JP)

(73) Assignee: PIGEON CORPORATION, Tokyo (JP)

( * ) Notice: Subject to any disclaimer, the term of this patent is extended or adjusted under 35 U.S.C. 154(b) by 945 days.

(21) Appl. No.: 17/055,232

(22) PCT Filed: May 13, 2019

(86) PCT No.: PCT/JP2019/018927
§ 371 (c)(1),
(2) Date: Nov. 13, 2020

(87) PCT Pub. No.: WO2019/221057
PCT Pub. Date: Nov. 21, 2019

(65) Prior Publication Data
US 2021/0213184 A1    Jul. 15, 2021

(30) Foreign Application Priority Data
May 15, 2018   (JP) .................................. 2018-094024

(51) Int. Cl.
*A61M 1/06*   (2006.01)
(52) U.S. Cl.
CPC .............. *A61M 1/06* (2013.01); *A61M 1/062* (2014.02); *A61M 2210/1007* (2013.01)
(58) Field of Classification Search
CPC .................... A61M 1/06; A61M 1/062; A61M 2210/1007; A61M 2205/586
See application file for complete search history.

(56) References Cited

U.S. PATENT DOCUMENTS 6,749,582 B2   6/2004 Britto et al.
2003/0204164 A1 * 10/2003 Britto .................... A61M 1/064
                                                           604/74

FOREIGN PATENT DOCUMENTS

CN   201370805 Y   12/2009
CN   203663144 U    6/2014
(Continued)

OTHER PUBLICATIONS

Notice of Second Office Action of the corresponding CN application 201980031478.1 mailed Jun. 9, 2023 and English translation thereof.
(Continued)

*Primary Examiner* — Lauren P Farrar
(74) *Attorney, Agent, or Firm* — Muncy, Geissler, Olds & Lowe, P.C.

(57) ABSTRACT

To provide a manual breast pump capable of stabilizing movement of a handle while reducing burden on muscle resulting from a repetitive operation of the handle. A manual breast pump 2 has a main body 3 having a passage 312 through which extracted breast milk passes, a hood 4 connected to the main body 3 and placed onto a breast, a diaphragm 34 generating a negative pressure in the passage 312, a holding member 200 attached to the main body 3 and provided to be rotatable with respect to the main body 3, and a handle 5 for being operated thereby deforming the diaphragm 34, the handle being held by the holding member 200. When the holding member 200 rotates with respect to the main body 3, the handle 5 rotates with respect to the main body 3 together with the holding member 200.

2 Claims, 12 Drawing Sheets

(56) References Cited

FOREIGN PATENT DOCUMENTS

| | | | |
|---|---|---|---|
| CN | 104918642 A | 9/2015 | |
| EP | 2186532 A1 | 5/2010 | |
| EP | 2875835 A1 * | 5/2015 | ............. A61M 1/06 |
| JP | 2005313124 A | 11/2005 | |

OTHER PUBLICATIONS

Office Action of the corresponding CN application No. 201980031478.1 mailed Nov. 21, 2022 and English translation thereof.
The extended European Search Report of EP19804176.6 mailed Jan. 4, 2022.

* cited by examiner

MANUAL BREAST PUMP

TECHNICAL FIELD

The present invention relates to a manual breast pump for manually extracting breast milk.

BACKGROUND ART

Conventionally, a manual breast pump with which a user manually extracts breast milk is known. Generally, a manual breast pump has a main body, a hood connected to the main body and placed onto a breast, a diaphragm connected to the main body and generating negative pressure in an internal space of the hood, and a handle for being operated thereby deforming the diaphragm, with the handle approaching to and separating from the main body. The placement of handle to the main body is typically implemented in a fixed manner. In other words, the handle performs a reciprocating motion of approaching to the main body and separates from the main body in a state where the placement thereof to the main body is fixed. Therefore, when the user places the hood onto a breast to extract breast milk using the manual breast pump, the placement of the handle is inevitably determined. As a result, the user may not be able to place a joint of a hand operating the handle at an intermediary position. Therefore, there is room for improvement to deal with burden on muscle caused due to the repetitive operation of the handle.

Here, PTL 1 discloses a manual breast pump that includes a suction cup forming an internal suction chamber, a breast shield expanding from the suction cup, and a manual operation lever provided to the suction cup. In the manual breast pump described in PTL 1, the manual operation lever can be disposed in a plurality of positions with respect to the suction cup, and can be operated periodically in each of the plurality of positions, and moreover generates negative pressure in the internal suction chamber. Furthermore, the manual operation lever is rotatable with respect to the suction cup.

CITATION LIST

Patent Literature

[PTL 1] U.S. Pat. No. 6,749,582 (Specification)

SUMMARY OF INVENTION

Technical Problem

However, the manual breast pump described in PTL 1 has a problem in which the rotation mechanism of the operation manual lever is complicated. In addition, the height position for supporting the reciprocating motion of the manual operation lever and the height position of the rotation mechanism of the operation manual lever are substantially the same. Therefore, when the user repeatedly operates or rotates the manual operation lever, movement of the operation manual lever becomes unstable. As a result, the user cannot operate the handle stably, making it difficult for the user to implement operation of breast milk extraction easily. Therefore, a manual breast pump that can stabilize movement of the handle while reducing the burden on the muscle resulting from the repetitive operation of the handle has been desired.

The present invention was contrived in order to solve the foregoing problems, and an object thereof is to provide a manual breast pump capable of stabilizing movement of a handle while reducing the burden on muscle resulting from a repetitive operation of the handle.

Solution to Problem

According to the present invention, the problems are solved by a manual breast pump including: a main body having a passage through which extracted breast milk passes; a hood connected to the main body and placed onto a breast; a diaphragm provided to the main body and generating a negative pressure in the passage; a holding member attached to the main body and provided so as to be rotatable with respect to the main body; and a handle for being operated thereby deforming the diaphragm, the handle being held by the holding member, wherein when the holding member rotates with respect to the main body, the handle rotates with respect to the main body together with the holding member.

According to this configuration, the handle is held by the holding member. The holding member is attached to the main body and provided so as to be rotatable with respect to the main body. The handle rotates along with the holding member with respect to the main body when the holding member rotates with respect to the main body. Therefore, when a user places the hood onto a breast, the user can rotate the position of the handle with respect to the main body and thereby adjust the handle to a position preferable for a repetitive operation of the handle. Consequently, the burden on the muscle resulting from the repetitive operation of the handle can be reduced.

Further, the handle is held by the holding member that is attached so as to be rotatable with respect to the main body, and rotates along with the holding member. Therefore, a complicated rotation mechanism for rotating the handle is not necessary. In other words, the rotation mechanism of the handle can be simplified. Thus, movement of the handle can be stabilized. Consequently, the user can operate the handle stably and extract breast milk easily.

In the manual breast pump according to the present invention, it is preferred that the holding member include an attachment portion fitted therein so as to be rotatable with respect to the main body, and an extension portion extending from the attachment portion and supporting the handle in a reciprocable manner.

According to the foregoing configuration, the attachment portion of the holding member is fitted so as to be rotatable with respect to the main body. Furthermore, the extension portion of the holding member extends from the attachment portion and supports the handle in a reciprocable manner. Therefore, the extension portion for supporting the handle in a reciprocable manner extends from the attachment portion fitted rotatably in the main body, and is provided away from the attachment portion. Specifically, a part that rotates with respect to the main body (the attachment portion) and a part that supports the handle in a reciprocable manner (the extension portion) are arranged away from each other. In this manner, the stability of the rotation mechanism of the handle is ensured. Accordingly, movement of the handle (rotational operation and reciprocating motion) can be stabilized.

In the manual breast pump according to the present invention, it is preferred that the main body have a diaphragm mounting portion above which the diaphragm mounted, and a receiving portion provided in a position downwardly away from the diaphragm mounting portion, and that the attachment portion be installed in a sandwiched position between the diaphragm mounting portion and the receiving portion.

According to this configuration, the attachment portion of the holding member is installed in a sandwiched position between the diaphragm mounting portion having the diaphragm mounted thereabove and the receiving portion. In this case, the receiving portion is provided in a position away from the diaphragm mounting portion in a downward direction. Specifically, the attachment portion of the holding member is installed in a sandwiched position between the diaphragm mounting portion and the receiving portion that are away from each other in a vertical direction. Therefore, when the handle rotates with respect to the main body, the attachment portion of the holding member can rotate stably between the diaphragm mounting portion and the receiving portion. In other words, the rotational operation of the handle can be stabilized. In addition, since the attachment portion of the holding member is installed in a sandwiched position between the diaphragm mounting portion and the receiving portion, movement of the holding member that occur when the handle reciprocates can be suppressed. As a result, the reciprocating motion of the handle can be stabilized.

In the manual breast pump according to the present invention, it is preferred that the main body have a guide portion provided between the diaphragm mounting portion and the receiving portion, and that the attachment portion have a rotation stabilizing portion installed in a sandwiched position between the diaphragm mounting portion and the guide portion.

According to this configuration, the rotation stabilizing portion is installed in a sandwiched position between the diaphragm mounting portion and the guide portion provided between the diaphragm mounting portion and the receiving portion. Therefore, when the handle rotates with respect to the main body, the attachment portion of the holding member can rotate more stably between the diaphragm mounting portion and the receiving portion.

In the manual breast pump according to the present invention, it is preferred that the main body have a rotation angle regulating portion that regulates a range of rotation angle of the holding member when the holding member rotates with respect to the main body.

According to this configuration, the rotation angle regulating portion regulates the range of rotation angle of the holding member with respect to the main body. Thus, the range of rotation angle of the handle held by the holding member and rotating along with the holding member is regulated by the rotation angle regulating portion of the main body. Thus, the user can reliably recognize the range of rotation of the handle attached to the holding member, and thereby adjust the handle to an arbitrary position with ease after understanding the range of rotation of the handle.

Advantageous Effects of Invention

The present invention can provide a manual breast pump capable of stabilizing movement of the handle while reducing the burden on the muscle resulting from the repetitive operation of the handle.

DESCRIPTION OF EMBODIMENTS

Figure 1:
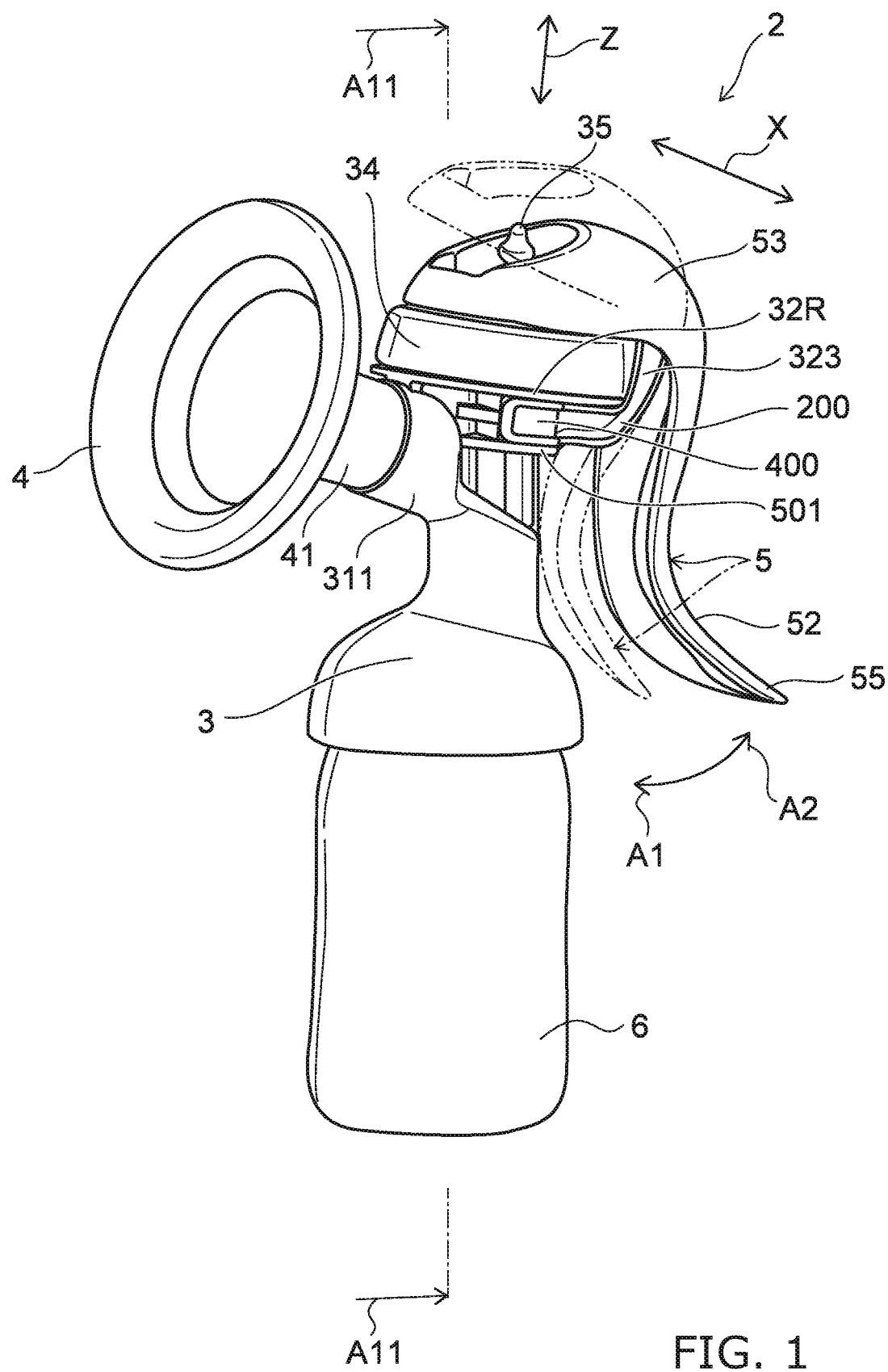
FIG. 1 is a perspective view illustrating a manual breast pump according to an embodiment of the present invention.

Preferred embodiments of the present invention are now described hereinafter in detail with reference to the drawings.

Note that, since the embodiments described below are favorable specific examples of the present invention, various technically favorable limits are applied thereto; however, the scope of the present invention is not limited to these embodiments unless the following description states that the present invention is particularly limited. Further, in each drawing, identical components are designated the same reference numerals; thus, detailed descriptions thereof are omitted accordingly.

A manual breast pump according to the present embodiment is now described with reference to FIGS. 1 to 3. The manual breast pump 2 according to the present embodiment (simply referred to as "breast pump" for convenience, in the following description) is a tool that can be operated manually by a user to extract breast milk, and is used when, for example, breast-feeding an infant directly is difficult or a nipple is damaged, or for the purpose of preventing mastitis. The user uses the breast pump 2 by holding the breast pump by hand. Therefore, it is preferred that the breast pump 2 be lightweight, capable of single-handed operation, and capable of reducing fatigue.

Figure 2:
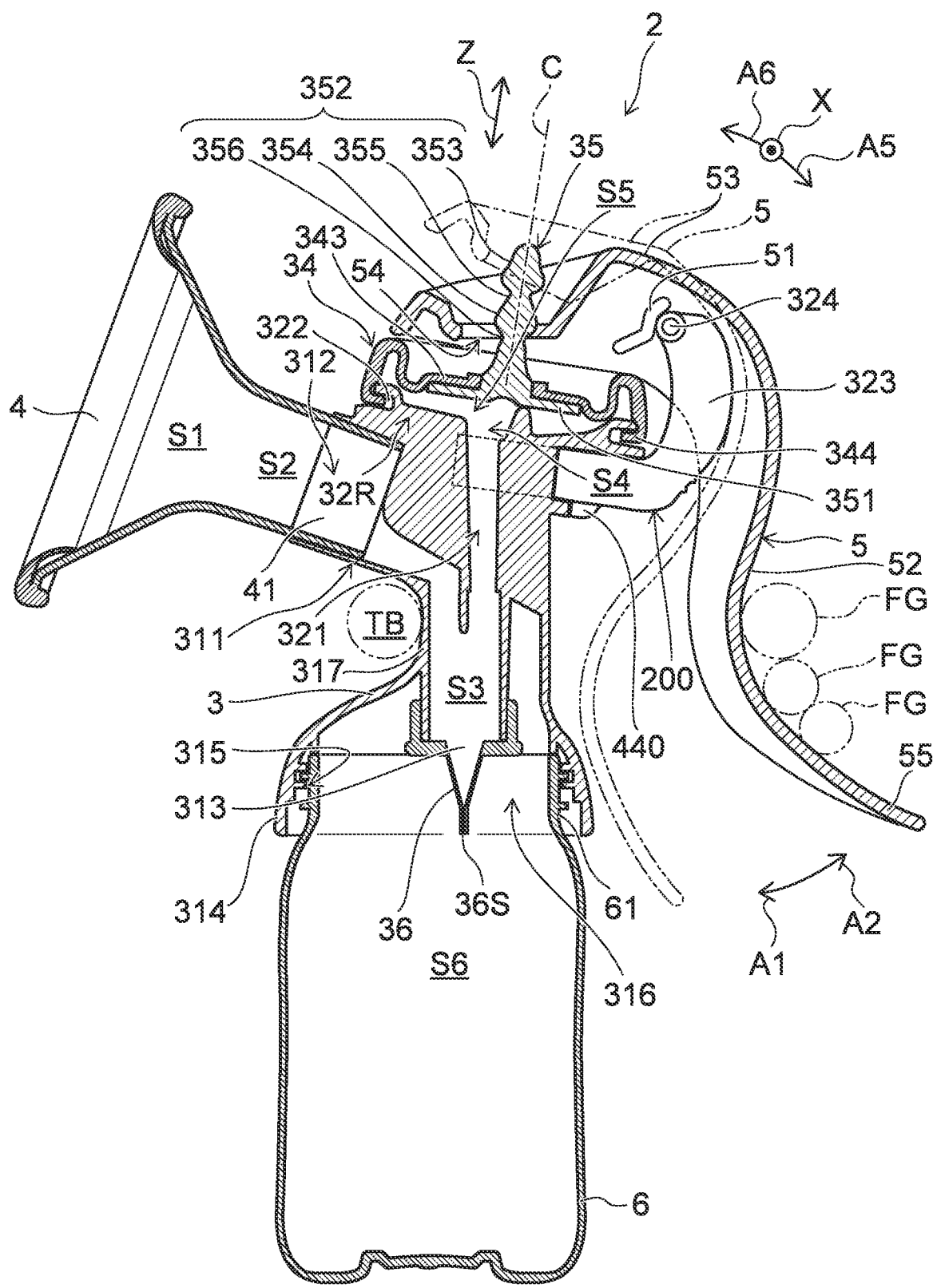
FIG. 2 is a cross-sectional view of the manual breast pump, taken along a cut surface A11-A11 shown in FIG. 1.

As shown in FIGS. 1 and 2, the breast pump 2 includes a main body 3, a hood 4, a diaphragm 34, a handle 5, and a holding member 200. The breast pump 2 may further have a bottle 6. The hood 4 is formed in the shape of a trumpet or in substantially a dome shape so as to correspond to the shape of a breast, and is placed onto the breast. A small diameter portion 41 having the smallest diameter in the hood 4 is connected to a mounting portion 311 provided in an upper portion of the main body 3. When a user inserts the breast into a space S1 surrounded by the hood 4 shown in FIG. 2, the space S1 creates a housing space S2 for housing a nipple of the user in such a manner as to seal the nipple. A structure that enables extraction of breast milk is formed by setting negative pressure in the housing space S2.

The main body 3 is relatively light, and is molded with a hard synthetic resin material. Examples of the material of the main body 3 include polypropylene, polycarbonate, polycycloolefin, polyethersulfone, and polyphenylsulfone. A first passage 312 through which air and extracted breast milk pass is formed inside the mounting portion 311 to which the hood 4 is mounted. As shown in FIG. 2, the first passage 312 is spatially connected to a communication portion S4 via an internal space S3 and a second passage 321 formed substantially in the middle of the main body 3, the communication portion S4 being formed in the upper portion of the main body 3. The internal space S3 is a breast milk storage space for temporarily storing the extracted breast milk. The first passage 312 of the present embodiment corresponds to the "passage" of the present invention.

The upper portion of the main body 3 is provided with the diaphragm 34 in a detachable manner. The diaphragm 34 is integrally molded with an elastic body such as a synthetic resin, and therefore has flexibility as a whole. A lower end portion 344 of the diaphragm 34 is attached to cover an outer periphery of a substantially disk-shaped diaphragm mounting portion 32R provided in the upper portion of the main body 3. Specifically, the diaphragm 34 is mounted above the diaphragm mounting portion 32R of the main body 3.

A negative pressure space S5 formed between the main body 3 and the diaphragm 34 is a region (space) where negative pressure is applied. As a result of the diaphragm 34 changing the shape thereof along an axis C, the negative pressure space S5 formed between the main body 3 and the diaphragm 34 enters a negative pressure state. The axis C represents an axial direction of a joint portion 35. The joint portion 35 will be described hereinafter in detail. When the negative pressure space S5 enters a negative pressure state, the housing space S2 enters a negative pressure state via the first passage 312, the internal space S3, the second passage 321, and the communication portion S4.

As shown in FIG. 2, an opening 313 is formed on the lower side of the internal space S3, and a backflow prevention valve 36 is attached thereto. For example, an on-off valve called duckbill valve is employed as the backflow prevention valve 36 of the present embodiment. However, the backflow prevention valve 36 is not limited to a duckbill valve. The backflow prevention valve 36 efficiently enables the negative pressure state of the housing space S2 by preventing the breast milk and air passing through the opening 313 from flowing back from the bottle 6. The backflow prevention valve 36 is molded integrally using an elastic body such as a synthetic resin, and therefore has flexibility as a whole. Examples of the material of the backflow prevention valve 36 include silicone rubber, elastomer, and natural rubber.

The backflow prevention valve 36 shown in FIG. 2 has a slit 36S at a tip thereof. The slit 36S closes as soon as the negative pressure space S5 enters a negative pressure state. Specifically, when the negative pressure space S5 enters a negative pressure state, the internal space S3 enters a negative pressure state through the communication portion S4 and the second passage 321. As a result, the slit 36S of the backflow prevention valve 36 closes. Consequently, the housing space S2 can enter a negative pressure state via the first passage 312, while the internal space S3 ensures high sealability thereof.

Furthermore, in a state where the breast milk is stored in the slit 36S and the internal space S3, when the negative pressure state of the negative pressure space S5 is removed, the slit 36S of the backflow prevention valve 36 is opened by the volume of the breast milk and the removal of the negative pressure (changing to a constant pressure), guiding the stored breast milk to a space S6 inside the bottle 6. As shown in FIG. 2, the main body 3 has, at a lower end portion thereof, a detachable portion 314 provided so as to be detachable with respect to the bottle 6. The detachable portion 314 is in a dome shape or a cylindrical shape. The space S6 inside the bottle 6 is communicated with the internal space S3 when the backflow prevention valve 36 opens the opening 313.

As shown in FIG. 2, a female screw portion 315 is provided inside the detachable portion 314. On the other hand, a male screw portion 61 is provided on the outside of an upper end portion of the bottle 6. The female screw portion 315 of the detachable portion 314 and the male screw portion 61 of the bottle 6 can be screwed to each other. Note that the bottle 6 may be a special product designed for the breast pump 2 or a baby bottle or the like applicable to the detachable portion 314. In addition, the bottle 6 does not have to be a molded container and may be a bag.

The diaphragm 34 shown in FIG. 2 is a negative pressure generating member for generating a negative pressure. In the present embodiment, the diaphragm 34 is connected to the diaphragm mounting portion 32R provided in the upper portion of the main body 3. By mounting the diaphragm 34 to the diaphragm mounting portion 32R, the negative pressure space S5 is formed between the main body 3 and the diaphragm 34.

The diaphragm 34 is formed of a relatively elastic, soft deformable material, that is, a synthetic resin having a hardness of approximately HS 30 to 70 according to type A durometer in JIS-K 6253 (ISO 7619). Examples of the material of the diaphragm 34 include silicone rubber, isoprene rubber, elastomers such as SEBS (styrene-ethylene-butylene-styrene). In the present embodiment, silicone rubber is used as the material of the diaphragm 34.

As shown in FIG. 2, a lower portion of the joint portion 35 is attached to a bottom surface portion 343 of the diaphragm 34, and an upper portion of the same is coupled to the handle 5. The diaphragm 34 is deformed when receiving, at the bottom surface portion 343, the effect of a reciprocating motion of the handle 5 via the joint portion 35. As a result, the bottom surface portion 343 is pulled up by the joint portion 35, changing the space volume of the negative pressure space S5 formed between the bottom surface portion 343 and the upper portion of the main body 3. Consequently, the diaphragm 34 applies a certain amount of negative pressure to the negative pressure space S5. Specifically, the deformation of the diaphragm 34 results in the negative pressure state of the negative pressure space S5. When the negative pressure space S5 enters the negative pressure state, the air inside the first passage 312 is sucked through the communication portion S4, the second passage 321, and the internal space S3, thereby sucking (extracting) the breast milk.

The joint portion 35 is formed of a material harder than the material of the diaphragm 34. Examples of the material of the joint portion 35 include polypropylene, polycarbonate, polycycloolefin, polyethersulfone, and other synthetic resins. The joint portion 35 has a flat disk-shaped base portion 351. The base portion 351 is disposed under the bottom surface portion 343 (the negative pressure space S5 side).

Further, the joint portion 35 has a coupling portion 352 protruding upward from the base portion 351 and extending in the shape of an axis. The coupling portion 352 is coupled detachably to the handle 5. Specifically, the coupling portion 352 can be coupled to the handle 5 by being inserted into a through hole (having a diameter smaller than the base portion 351) formed in the middle of the bottom surface portion 343 of the diaphragm 34, and by being exposed above the bottom surface portion 343. When the user pulls up the handle 5 coupled to the coupling portion 352, the base portion 351 pulls up the bottom surface portion 343 of the diaphragm 34. As a result, the diaphragm 34 is deformed, enlarging the negative pressure space S5. Note that the base portion 351 of the present embodiment is disposed without being connected to the bottom surface portion 343, under the bottom surface portion 343 of the diaphragm 34. However, how the base portion 351 is installed is not limited to the foregoing manner. For example, the base portion 351 may be fixed above the bottom surface portion 343.

As shown in FIG. 2, the coupling portion 352 has a first protrusion 353 and a second protrusion 354 arranged side by side along a stretching direction Z of the coupling portion 352. The first protrusion 353 and the second protrusion 354 each protrude radially from a shaft portion of the coupling portion 352. A first engaging portion 355 is provided between the first protrusion 353 and the second protrusion 354. The first engaging portion 355 is a part recessed (groove portion) between the first protrusion 353 and the second protrusion 354. Also, a second engaging portion 356 is provided between the second protrusion 354 and the base portion 351. The second engaging portion 356 is a portion recessed (groove portion) between the second protrusion 354 and the base portion 351.

The holding member 200 is attached to the main body 3 and provided so as to be rotatable with respect to the main body 3. For example, the holding member 200 rotates about an axis perpendicular to a lower surface of the diaphragm mounting portion 32R. The axis C shown in FIG. 2 is the axial direction of the joint portion 35 as described above, and is an example of the axis perpendicular to the lower surface of the diaphragm mounting portion 32R in a state obtained prior to the deformation of the diaphragm 34. Note that, as long as the holding member 200 is provided so as to be rotatable with respect to the main body 3, a rotary shaft of the holding member 200 is not limited to the axis C shown in FIG. 2. As shown in FIG. 1, the holding member 200 has an attachment portion 400 and an extension portion 323. The attachment portion 400 is installed in a sandwiched position between the diaphragm mounting portion 32R and a receiving portion 501 and fitted so as to be rotatable with respect to the main body 3. The receiving portion 501 is provided in the main body 3, at a position away from the diaphragm mounting portion 32R in a downward direction. Specifically, the main body 3 has the receiving portion 501 provided at a position that is away from the diaphragm mounting portion 32R in the downward direction. In the direction along the axis C in the state obtained prior to the deformation of the diaphragm 34, since the gap between the receiving portion 501 and the diaphragm mounting portion 32R is substantially the same as or slightly wider than the width of the attachment portion 400, the attachment portion 400 is restricted by both the receiving portion 501 and the diaphragm mounting portion 32R from moving in the direction along the axis C. Thus, the rotation of the holding member 200 is stabilized. The extension portion 323 extends from the attachment portion 400, to support the handle 5 in a reciprocable manner. The holding member 200 will be described hereinafter in detail.

The handle 5 shown in FIG. 2 is held by the holding member 200 and supported so as to be reciprocable with respect to the extension portion 323 of the holding member 200. Specifically, the handle 5 can reciprocate in the direction of arrows A1 and A2 shown in FIGS. 1 and 2. The handle 5 is detachably coupled to the coupling portion 352 by coming into engagement with the first engaging portion 355 or the second engaging portion 356. Therefore, the position in the stretching direction Z where the handle 5 and the coupling portion 352 are coupled to each other can be changed. Accordingly, the distance at which the handle 5 pulls up the coupling portion 352 can be changed. Thus, the amount of deformation of the diaphragm 34 can be changed. Specifically, as shown in FIG. 2, the first engaging portion 355 and the second engaging portion 356 are formed in the form of steps, away from each other in the stretching direction Z. Thus, the distance at which the handle 5 pulls up the coupling portion 352 can be changed stepwise in accordance with the engagement position between the handle 5 and the engaging portions 355, 356.

When the handle 5 shown in FIG. 2 comes into engagement with the first engaging portion 355, the distance at which the handle 5 pulls up the coupling portion 352 is shorter than when the handle 5 comes into engagement with the second engaging portion 356. Consequently, the change in space volume of the negative pressure space S5 is relatively small. Therefore, the handle 5 and the diaphragm 34 generate a relatively low negative pressure in the negative pressure space S5 and return to the original states thereof in a relatively short period of time (preparation mode). On the other hand, when the handle 5 comes into engagement with the second engaging portion 356, the distance at which the handle 5 pulls up the coupling portion 352 is longer than when the handle 5 comes into engagement with the first engaging portion 355. Consequently, the change in space volume of the negative pressure space S5 is relatively large. Therefore, the handle 5 and diaphragm 34 generate a relatively high negative pressure in the negative pressure space S5 and return to the original states thereof over a relatively long period of time (extraction mode).

The handle 5 has a long shape and, as a whole, is molded using a relatively hard, lightweight synthetic resin. Examples of the material of the handle 5 include polypropylene, polycarbonate, polycycloolefin, and polyethersulfone. The handle 5 is disposed above the diaphragm 34 and has a lift portion 53 for lifting up the diaphragm 34, and a lever portion 52 that is bent from the lift portion 53 and located on a side surface of the main body 3.

Figure 3:
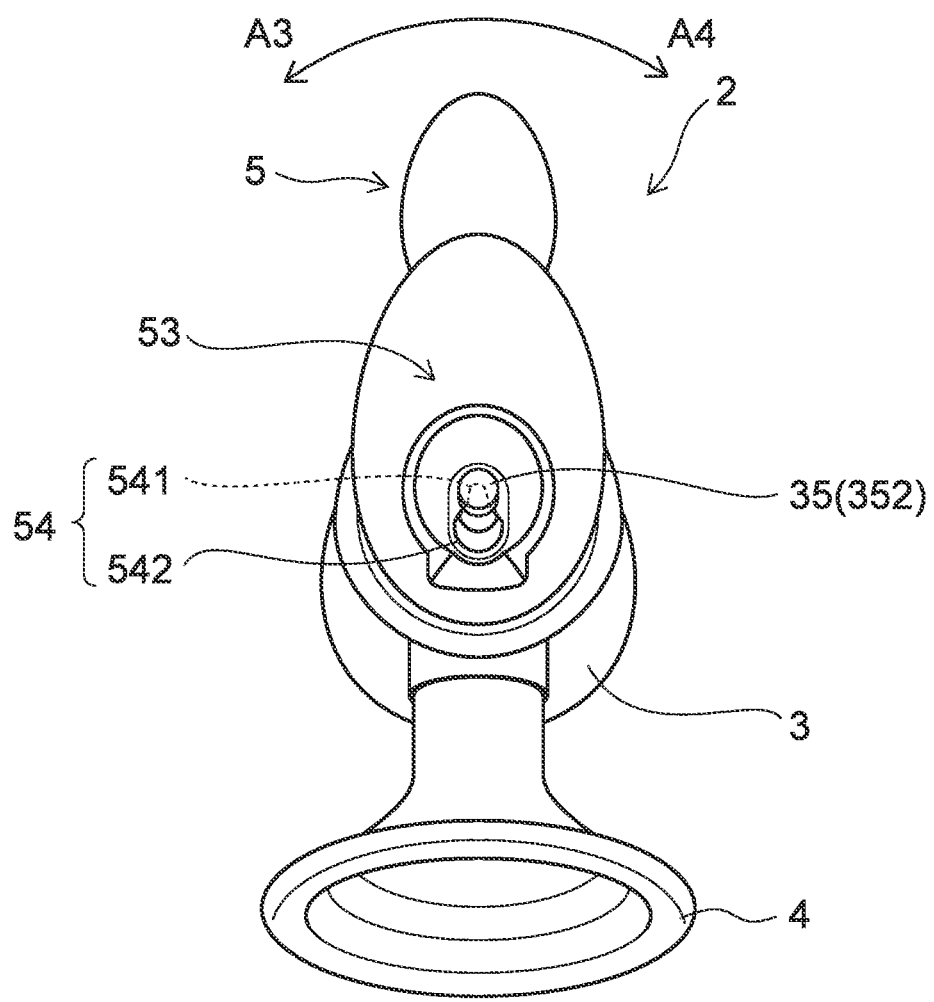
FIG. 3 is a plan view of the manual breast pump of the present embodiment as viewed from above.

As shown in FIG. 3, the lift portion 53 is provided with a coupled portion 54 that is coupled to the coupling portion 352. The coupled portion 54 has a holding opening 541 for holding a coupling position of the coupling portion 352, and an insertion opening 542 through which the coupling portion 352 is inserted. The holding opening 541 and the insertion opening 542 are spatially connected to each other.

The inner diameter of the holding opening 541 is slightly larger than the outer diameters of the first engaging portion 355 and the second engaging portion 356 shown in FIG. 2, but is smaller than the outer diameters of the first protrusion 353 and the second protrusion 354. On the other hand, the inner diameter of the insertion opening 542 is larger than the outer diameters of the first protrusion 353 and the second protrusion 354 shown in FIG. 2. Therefore, after inserting the coupling portion 352 into the insertion opening 542, the user can position the handle 5 and the coupling portion 352 to each other by sliding the coupling portion 352 toward the holding opening 541 to place the first engaging portion 355 or the second engaging portion 356 in the holding opening 541.

As shown in FIG. 2, the lever portion 52 is formed into the shape of a lever and functions as a handle. A region outside the lever portion 52 corresponds to a region where the user puts her finger FG other than her thumb. That is, an outer surface of the lever portion 52 corresponds to a surface on which the user places the finger FG other than her thumb. The distance between the outer surface of the lever portion 52 on which the user places the finger FG and a recess portion 317 in the main body 3 on which the user places her thumb TB is the distance that the user can grab, with the main body 3 sandwiched between the outer surface of the lever portion 52 and the recess portion 317.

When the user holds the hand grabbing the main body 3, the lever portion 52 is pushed against the main body 3 and therefore approaches the main body 3. Consequently, the handle 5 rotates around a spindle portion 324 of the holding member 200 (see FIG. 2). As a result, the lift portion 53 of the handle 5 lifts up the diaphragm 34 via the joint portion 35. Subsequently, the space volume of the negative pressure space S5 increases, resulting in the negative pressure state. Thus, the housing space S2 enters a negative pressure state via the communication portion S4, the second passage 321, the internal space S3, and the first passage 312. The breast milk is extracted in this manner.

As shown in FIG. 2, the lever portion 52 is curved gradually toward the outside as the lever portion 52 stretches downward from the region where the finger FG is placed. Therefore, a lower end portion 55 of the handle 5 is shaped so as to curl slightly toward the outside. Therefore, when the user brings the lever portion 52 close to the main body 3, the finger FG can prevent the handle 5 from being shifted downward.

In a case where, for example, the placement of the handle with respect to the main body is fixed, the handle performs a reciprocating motion in which the handle moves toward or away from the main body in a state in which the placement of the handle with respect to the main body is fixed. In this case, therefore, when the user places the hood onto the breast in order to extract breast milk using the breast pump, the placement of the handle is inevitably determined. In such a case, the user may not be able to place the joint of the hand operating the handle, in the middle. Therefore, there is room for improvement in that the burden on the muscle is caused due to the repetitive operation of the handle.

On the other hand, the handle 5 of the breast pump 2 according to the present embodiment rotates along with the holding member 200 with respect to the main body 3 as shown by arrows A3 and A4 shown in FIG. 3, when the holding member 200 rotates with respect to the main body 3. At this moment, a complicated rotation mechanism for rotating the handle 5 is not necessary. Specifically, the rotation mechanism of the handle 5 can be simplified. The rotation mechanism of the handle 5 and movement of the handle 5 are further described hereinafter with reference to the drawings.

An attachment structure between the holding member 200 and the main body 3 and the rotation mechanism of the handle 5 are now described with reference to FIGS. 4 to 8. In addition, structural examples of the holding member 200 of the present embodiment are described with reference to FIGS. 9 and 10.

Figure 9:
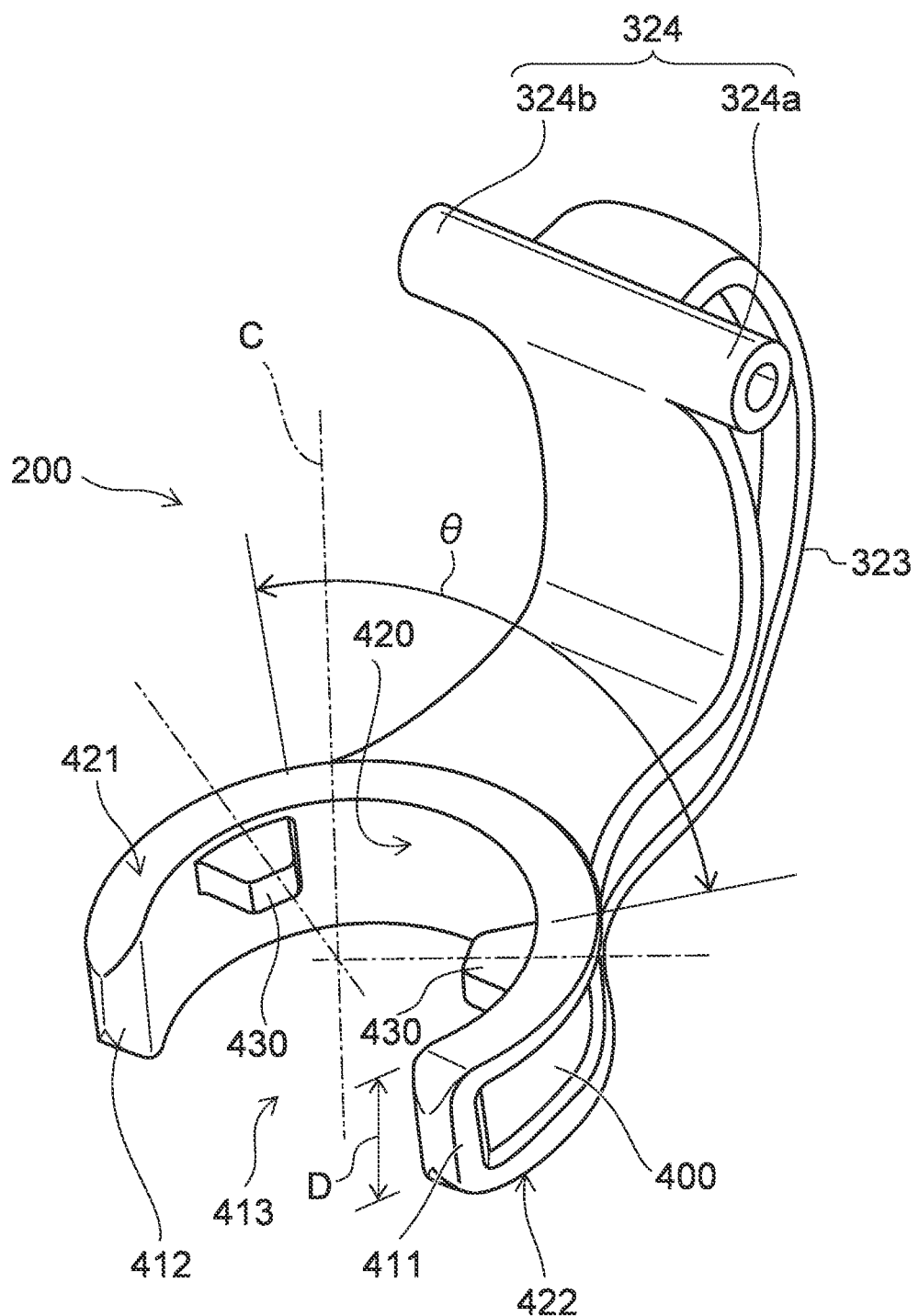
FIG. 9 is a perspective view showing a holding member of the present embodiment.
Figure 10:
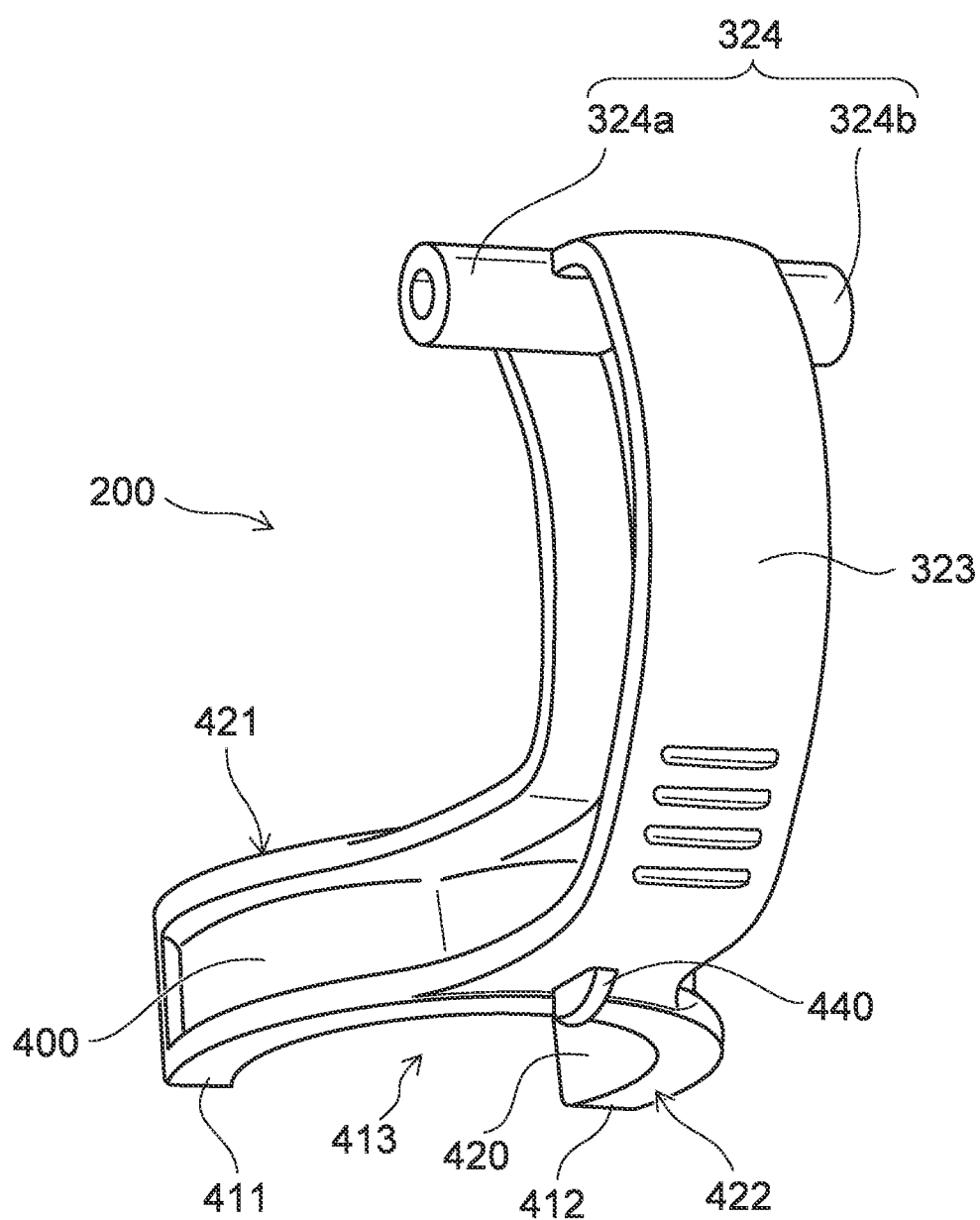
FIG. 10 is a perspective view showing the holding member of the present embodiment.

As shown in FIGS. 9 and 10, the holding member 200 has the attachment portion 400 and the extension portion 323 and is molded with a relatively hard, lightweight synthetic resin. Examples of the material of the holding member 200 include polypropylene, polycarbonate, polycycloolefin, and polyethersulfone.

The attachment portion 400 is formed into an arc shape and has a first end portion 411 and a second end portion 412. A cutout portion 413 is formed between the first end portion 411 and the second end portion 412. A space for housing an outer peripheral portion 32T of the main body 3 between the diaphragm mounting portion 32R and the receiving portion 501 is formed inside the attachment portion 400. The gap between the first end portion 411 and the second end portion 412 (spacing of the cutout portion 413) is set to a distance that enables the passage of the outer peripheral portion 32T of the main body 3 therethrough while the first end portion 411 and the second end portion 412 deform elastically when the attachment portion 400 of the holding member 200 is fitted into the main body 3. Therefore, as a result of the elastic deformation of the first end portion 411 and the second end portion 412 and therefore the widening of the cutout portion 413, the outer peripheral portion 32T of the main body 3 passes through the cutout portion 413 and is housed inside the attachment portion 400. In this manner, the attachment portion 400 of the holding member 200 is fitted in the main body 3.

As shown in FIG. 9, an inner peripheral portion (inner peripheral surface) 420 of the attachment portion 400 is formed into a circular curved surface, and faces the outer peripheral portion 32T of the main body 3 in a state where the holding member 200 is attached to the main body 3. Two guide projections 430 and 430 are formed on the inner peripheral portion 420 of the attachment portion 400 in such a manner as to protrude toward an internal space of the attachment portion 400. The guide projections 430 of the present embodiment correspond to an example of a "rotation stabilizing portion" of the present invention.

The attachment portion 400 has an upper surface 421 and a lower surface 422. A distance D between the upper surface 421 and the lower surface 422 (the thickness of the attachment portion 400) is substantially equal to or slightly shorter than a gap E between the diaphragm mounting portion 32R and the receiving portion 501 (see FIG. 6). The receiving portion 501 is provided in the main body 3, is formed into a substantially circular shape, and is parallel to the lower surface of the diaphragm mounting portion 32R.

Figure 5:
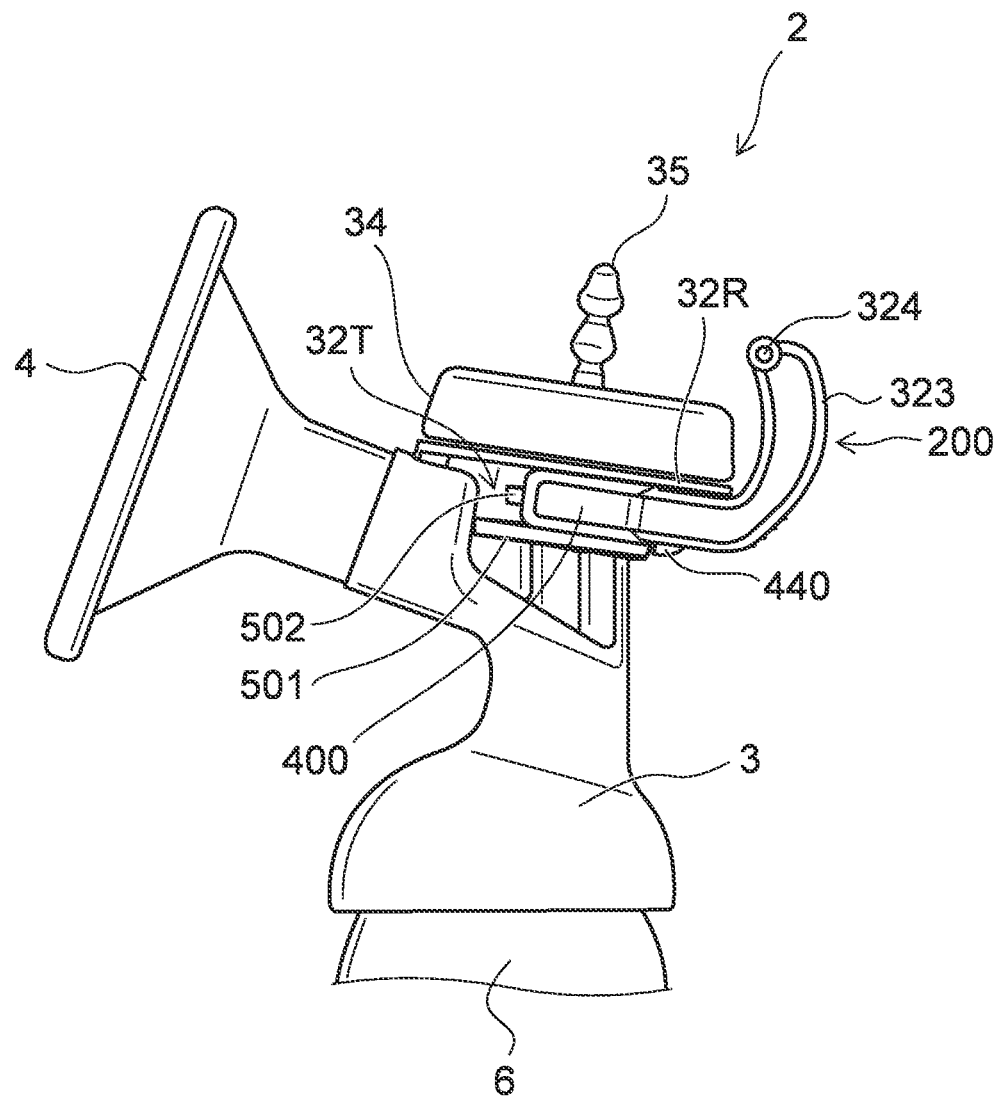
FIG. 5 is a plan view of the surroundings of the main body of the present embodiment as viewed from the side.

As shown in FIG. 5, the extension portion 323 passes the side of the diaphragm 34 in the state where the holding member 200 is attached to the main body 3, and extends from the attachment portion 400 so as to extend toward the upper side of the diaphragm 34 (in substantially the Z direction).

As shown in FIG. 9, one end portion of the extension portion 323 (upper end portion) is provided with the spindle portion 324. The spindle portion 324 has both end portions 324a, 324b. The both end portions 324a, 324b are detachably connected to a bearing portion 51 provided inside the handle 5 (see FIG. 2). Thus, as shown by the arrows A1 and A2 in FIGS. 1 and 2, the handle 5 can rotate around the spindle portion 324 of the holding member 200 with respect to the spindle portion 324 (in the direction of the arrows A5 and A6 shown in FIG. 2).

Figure 4:
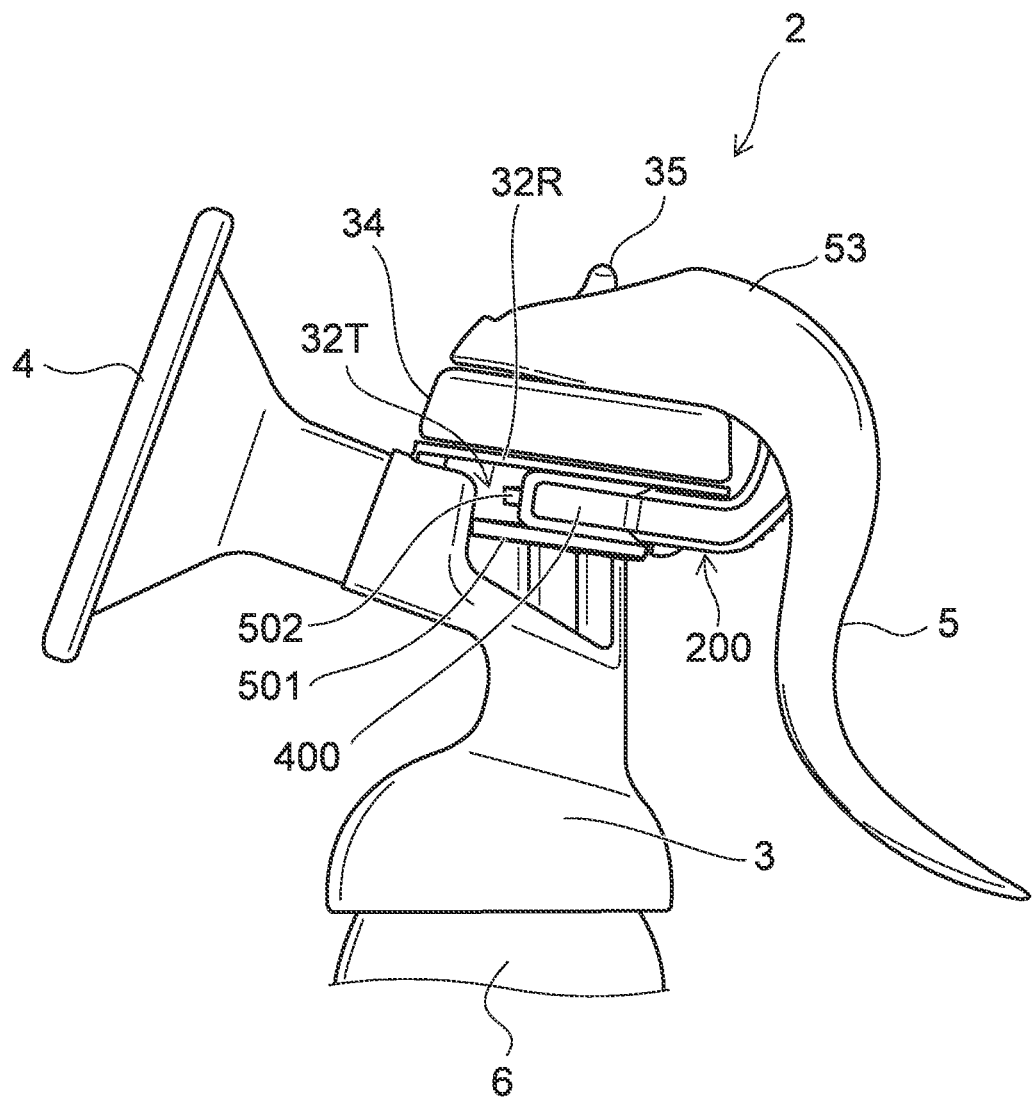
FIG. 4 is a plan view of the surroundings of a main body of the present embodiment as viewed from the side.

As shown in FIG. 10, a lower portion of the extension portion 323 is provided with a projection 440. In the extension portion 323, the projection 440 is provided in the vicinity of a boundary portion between the attachment portion 400 and the extension portion 323. As shown in FIGS. 4 and 5, the projection 440 is a part that approaches the main body 3 in the state where the holding member 200 is attached to the main body 3. For example, when the holding member 200 is about to be fitted, upside down, into the main body 3 (in a state where the extension portion 323 extends downward from the attachment portion 400), the projection 440 comes into contact with the diaphragm mounting portion 32R to function as an inversion prevention portion.

The holding member 200 is a member separate from the main body 3, and is detachably attached to the main body 3, as shown in FIGS. 4 to 8. Specifically, the attachment portion 400 of the holding member 200 is installed in a sandwiched position between the diaphragm mounting portion 32R and the receiving portion 501, and is detachably fitted to an outer peripheral portion of a guide portion 502 provided in the outer peripheral portion 32T of the main body 3.

Figure 6:
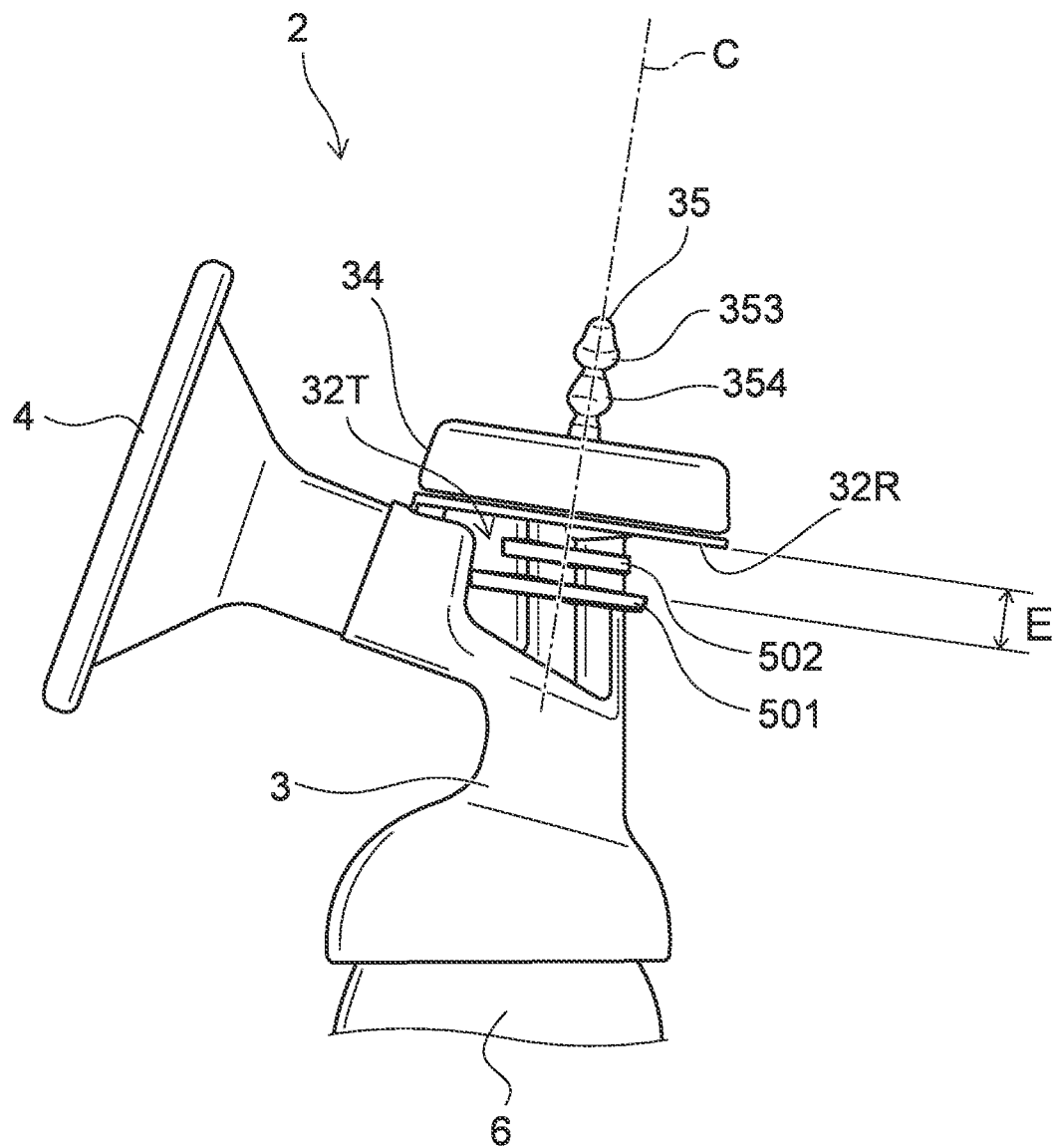
FIG. 6 is a plan view of the surroundings of the main body of the present embodiment as viewed from the side.
Figure 7:
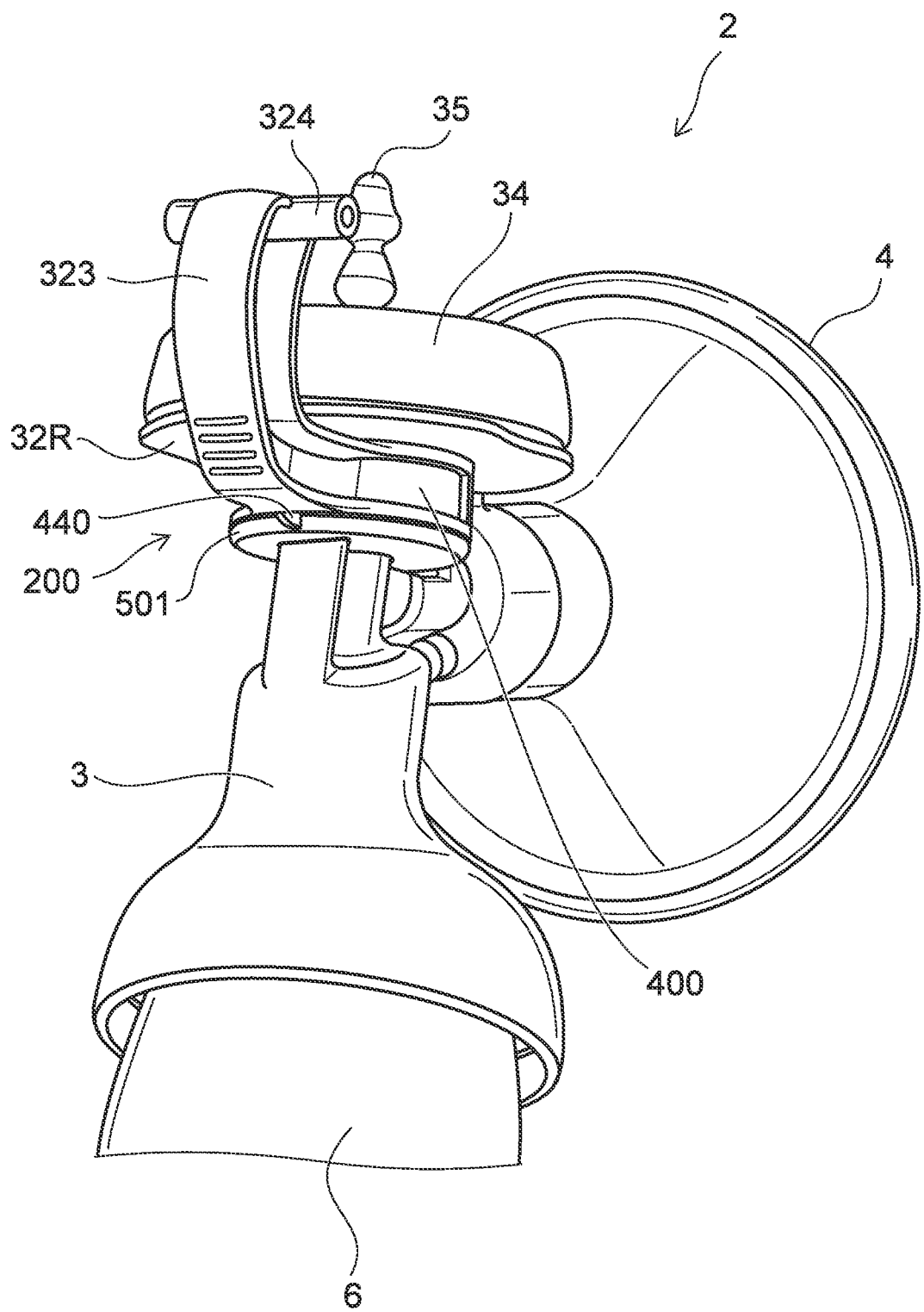
FIG. 7 is a perspective view showing the surroundings of the main body of the present embodiment.
Figure 8:
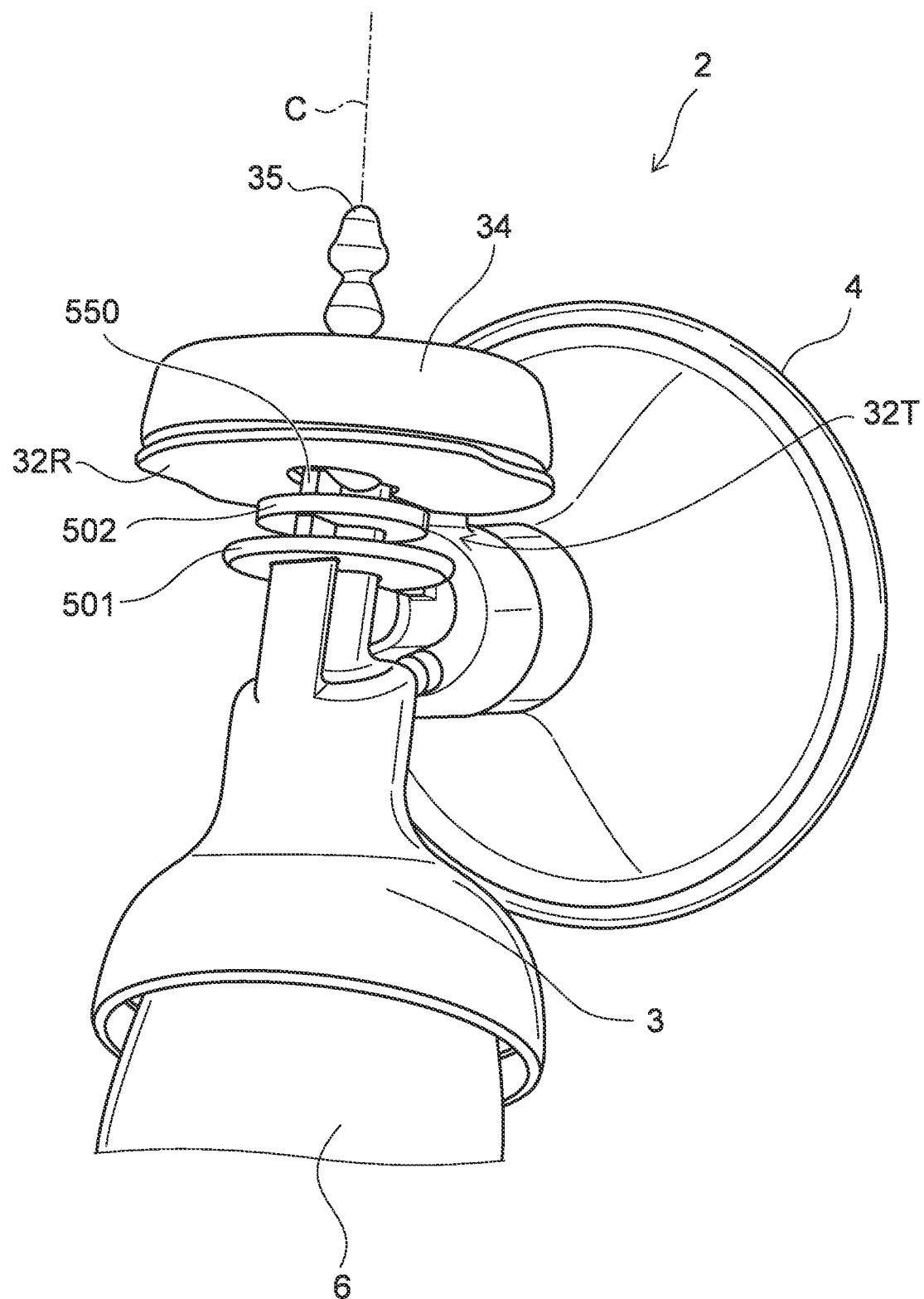
FIG. 8 is a perspective view showing the surroundings of the main body of the present embodiment.

As shown in FIGS. 6 and 8, the main body 3 has the guide portion 502 provided between the diaphragm mounting portion 32R and the receiving portion 501. The guide portion 502 is provided in the outer peripheral portion 32T of the main body 3 at a middle portion between the diaphragm mounting portion 32R and the receiving portion 501, and is formed in an approximately circular shape. The guide portion 502 is formed concentrically with the receiving portion 501, and is formed parallel to the receiving portion 501. The diameter of the receiving portion 501 is greater than the diameter of the guide portion 502 and smaller than the diameter of the diaphragm mounting portion 32R. The diameter of the guide portion 502 is smaller than the respective diameters of the receiving portion 501 and the diaphragm mounting portion 32R.

In the state where the holding member 200 is attached to the main body 3, the guide projections 430 are fitted in a space between the diaphragm mounting portion 32R and the guide portion 502. The guide projections 430 are guided to the guide portion 502, to stabilize the rotation of the holding member 200 with respect to the main body 3.

Figure 11:
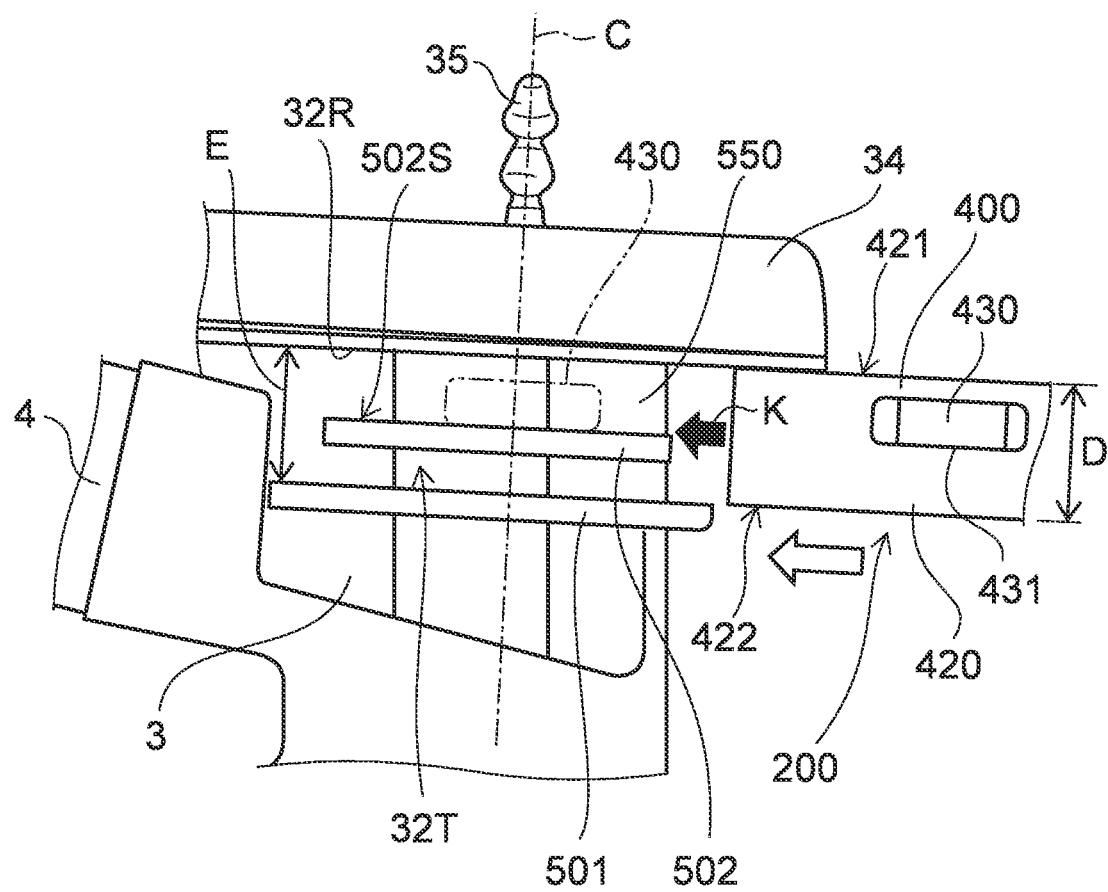
FIG. 11 is a plan view showing how the holding member of the present embodiment is fitted into the main body.

How the holding member 200 is fitted into the main body 3 is described next with reference to FIG. 11. As shown in FIG. 11, the attachment portion 400 of the holding member 200 is detachably fitted between the diaphragm mounting portion 32R and the receiving portion 501. In so doing, the upper surface 421 of the attachment portion 400 is guided along a K direction by the diaphragm mounting portion 32R. On the other hand, the lower surface 422 of the attachment portion 400 is guided along the K direction by the receiving portion 501. Therefore, the upper surface 421 of the attachment portion 400 is held or supported by the diaphragm mounting portion 32R. On the other hand, the lower surface 422 of the attachment portion 400 is held or supported by the receiving portion 501. Furthermore, a lower surface 431 of each guide projection 430 is guided in the K direction along an upper surface 502S of the guide portion 502.

Thus, the attachment portion 400 of the holding member 200 is securely held with respect to the outer peripheral portion of the guide portion 502. In addition, the attachment portion 400 of the holding member 200 can stably rotate with respect to the outer peripheral portion of the guide portion 502. When removing the holding member 200 from the main body 3, the user simply needs to pull out the attachment portion 400 of the holding member 200 in the direction opposite to the K direction.

As shown in FIGS. 8 and 11, the outer peripheral portion 32T of the main body 3 has a rotation angle regulating portion 550. The rotation angle regulating portion 550 is formed substantially along the direction of the axis C, between the diaphragm mounting portion 32R and the receiving portion 501. On the other hand, as shown in FIG. 9, the guide projection 430 set an allowable rotation angle θ in the attachment portion 400 of the holding member 200. The allowable rotation angle θ represents a range in which the attachment portion 400 of the holding member 200 shown in FIG. 11 can rotate with respect to the main body 3.

In other words, when the attachment portion 400 of the holding member 200 rotates in one direction, the rotation of the attachment portion 400 in said direction is restricted by either one of the two guide projections 430 coming into abutment with the rotation angle regulating portion 550. Also, when the attachment portion 400 of the holding member 200 rotates in the other direction, the rotation of the attachment portion 400 in said direction is restricted by the other one of the two guide projections 430 coming into abutment with the rotation angle regulating portion 550. Consequently, the holding member 200 and the handle 5 shown in FIG. 2 can rotate with respect to the main body 3 by the allowable rotation angle θ shown in FIG. 9. In this manner, the rotation angle regulating portion 550 regulates the range of rotation angle of the holding member 200 when the holding member 200 rotates with respect to the main body 3.

When the holding member 200 and the handle 5 rotate with respect to the main body 3, the lower surfaces 431 of the guide projections 430 are guided along the upper surface 502S of the guide portion 502. Therefore, the attachment portion 400 of the holding member 200 can rotate stably with respect to the main body 3. In other words, the guide projections 430 each function as the rotation stabilizing portion for stabilizing the rotation of the attachment portion 400 of the holding member 200 with respect to the main body 3, improving the rotational stability of the holding member 200 and the handle 5.

Figure 12A:
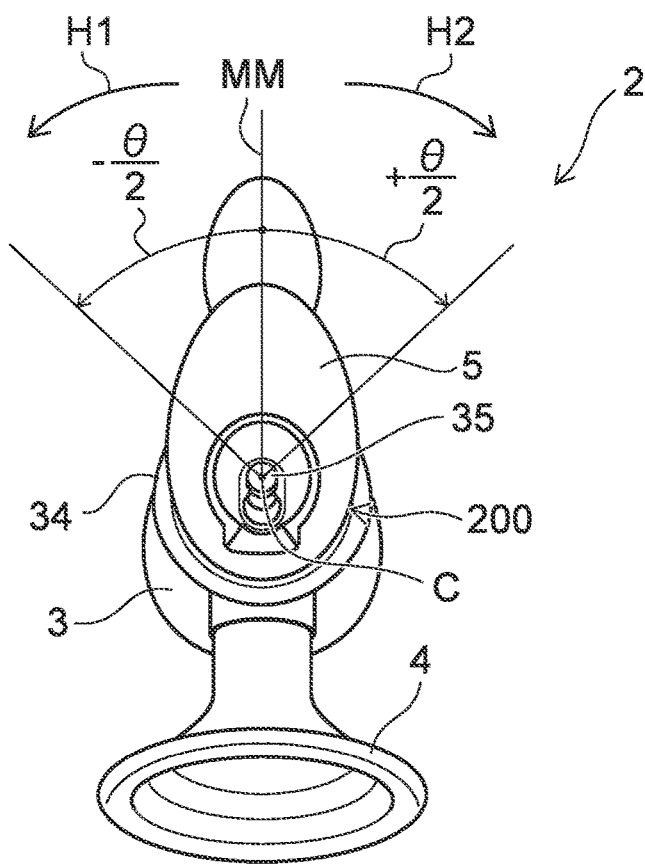
FIGS. 12(a)-12(c) are plan views showing how a handle of the present embodiment rotates with respect to the main body.
Figure 12B:
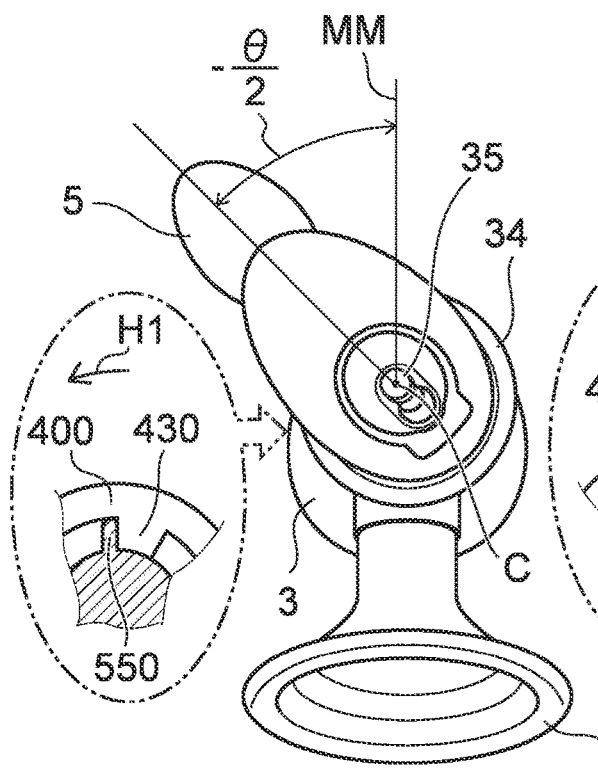
Figure 12C:
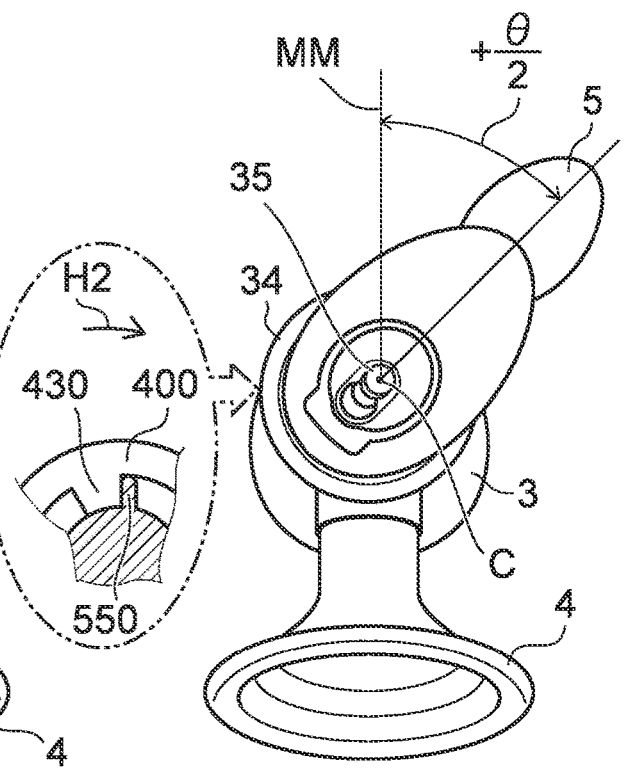

How the handle 5 rotates with respect to the main body 3 is described next with reference to FIGS. 12(a) to 12(c). As shown in FIG. 12(a), the handle 5 can rotate with respect to the main body 3 together with the holding member 200, in the direction of an arrow H1 from the middle position. As shown in FIG. 12(b), the rotation of the handle 5 is stopped by one of the guide projections 430 coming into abutment with the rotation angle regulating portion 550. The maximum rotation angle of the handle 5 at this moment is "−θ/2". Thus, the user can adjust the position (angle) of the handle 5 to the left side (the direction of the arrow H1) from a middle position MM.

Similarly, as shown in FIG. 12(a), the handle 5 can rotate with respect to the main body 3 together with the holding member 200, in the direction of an arrow H2 from the middle position. As shown in FIG. 12(c), the rotation of the handle 5 is stopped by the other guide projection 430 coming into abutment with the rotation angle regulating portion 550. The maximum rotation angle of the handle 5 at this moment is "+θ/2". Thus, the user can adjust the position (angle) of the handle 5 to the right side (the direction of H2) from the middle position MM.

In this manner, the holding member 200 and the handle 5 rotate with respect to the main body 3. The handle 5 is adjusted to an arbitrary position within the range of the allowable rotation angle θ shown in FIG. 12(a). In so doing, the range of the allowable rotation angle θ of the handle 5 is regulated by the rotation angle regulating portion 550 of the main body 3. Thus, the user can reliably recognize the range of rotation of the handle 5 attached to the holding member 200, and thereby adjust the handle 5 to an arbitrary position with ease after understanding the range of rotation of the handle 5. The allowable rotation angle θ is, for example, approximately 90 degrees. However, the allowable rotation angle θ is not limited to approximately 90 degrees, and can arbitrarily be set according to the installation position of the guide projections 430.

As described above, according to the breast pump 2 of the present embodiment, the handle 5 is held by the holding member 200. The holding member 200 is attached to the main body 3 and is provided so as to be rotatable with respect to the main body 3. When the holding member 200 rotates with respect to the main body 3, the handle 5 rotates along with the holding member 200, with respect to the main body 3. Therefore, when applying the hood 4 to the breast, the user can rotate the position of the handle 5 with respect to the main body 3, to adjust the handle 5 to a position preferable for the repetitive operation thereof. Consequently, the burden on the muscle resulting from the repetitive operation of the handle 5 can be reduced.

Further, the handle 5 is held by the holding member 200 which is attached so as to be rotatable with respect to the main body 3, and rotates along with the holding member 200. Therefore, a complicated rotation mechanism for rotating the handle 5 is not necessary. In other words, the rotation mechanism of the handle 5 can be simplified. Therefore, the movement of the handle 5 can be stabilized. Consequently, the user can operate the handle 5 stably and extract breast milk easily.

The attachment portion 400 of the holding member 200 is fitted in a rotatable manner with respect to the main body 3. Also, the extension portion 323 of the holding member 200 extends from the attachment portion 400, to support the handle 5 in a reciprocable manner. Therefore, the extension portion 323 that supports the handle 5 in a reciprocable manner extends from the attachment portion 400 that is fitted in a rotatable manner in the main body 3, and is away from the attachment portion 400. In other words, the part that rotates with respect to the main body 3 (the attachment portion 400) and the part that supports the handle 5 in a reciprocable manner (the extension portion 323) are arranged in the positions away from each other. Therefore, the stability of the rotation mechanism of the handle 5 is ensured. Accordingly, the movement of the handle 5 (rotational operation and reciprocating motion) can be stabilized.

In addition, the attachment portion 400 of the holding member 200 is installed in a sandwiched position between the diaphragm mounting portion 32R to which the upper diaphragm 34 is mounted and the receiving portion 501. In this case, the receiving portion 501 is provided in a position away from the diaphragm mounting portion 32R in the downward direction. Specifically, the attachment portion 400 of the holding member 200 is installed in a sandwiched position between the diaphragm mounting portion 32R and the receiving portion 501 that are away from each other in the vertical direction. Therefore, when the handle 5 rotates with respect to the main body 3, the attachment portion 400 of the holding member 200 can rotate stably between the diaphragm mounting portion 32R and the receiving portion 501. Specifically, the rotational operation of the handle 5 can be stabilized. In addition, since the attachment portion 400 of the holding member 200 is installed in a sandwiched position between the diaphragm mounting portion 32R and the receiving portion 501, the movement of the holding member 200 resulting from the reciprocating motion of the handle 5 can be suppressed. As a result, the reciprocating motion of the handle 5 can be stabilized.

The embodiments of the present invention have been described above. However, the present invention is not limited to the foregoing embodiments, and therefore various modifications can be made without departing from the scope of claims. The configurations of the foregoing embodiments can be partially omitted or arbitrarily combined so as to be different from the foregoing embodiments.

REFERENCE SIGNS LIST

2 Manual breast pump
3 Main body
4 Hood
5 Handle
6 Bottle
32R Diaphragm mounting portion
32T Outer peripheral portion
34 Diaphragm
36 Joint portion
36 Backflow prevention valve
36S Slit
41 Small diameter portion
51 Bearing portion
52 Lever portion
53 Lift portion
54 Coupled portion
55 Lower end portion
61 Male screw portion
200 Holding member
311 Mounting portion
312 First passage
313 Opening
314 Detachable portion
315 Female screw portion
316 Opening
317 Recess portion
321 Second passage
322 Groove portion
323 Extension portion
324 Spindle portion
324a, 324b End portion
343 Bottom surface portion
344 Lower end portion
351 Base portion
352 Coupling portion
353 First protrusion
354 Second protrusion
355 First engaging portion
356 Second engaging portion
400 Attachment portion
411 First end portion
412 Second end portion
413 Cutout portion
420 Inner peripheral portion
421 Upper surface
422 Lower surface
430 Guide projection
431 Lower surface
440 Projection
501 Receiving portion
502 Guide portion
502S Upper surface
541 Holding opening
542 Insertion opening
550 Rotation angle regulating portion
C Axis
E Gap
FG Finger
MM Middle position
S1 Space
S2 Housing space
S3 Internal space
S4 Communication portion
S5 Negative pressure space
S6 Space
TB Thumb
θ Allowable rotation angle

The invention claimed is:

1. A manual breast pump, comprising:
   a main body having a passage through which extracted breast milk passes;
   a hood connected to the main body and configured to be placed onto a breast;
   a diaphragm provided to the main body and generating a negative pressure in the passage;
   a holding member attached to the main body and provided to be rotatable with respect to the main body; and
   a handle for being operated thereby deforming the diaphragm, the handle being held by the holding member, wherein
   when the holding member rotates with respect to the main body, the handle rotates with respect to the main body together with the holding member,
   the holding member has:
      an attachment portion fitted to the main body so as to be rotatable with respect to the main body;
      an extension portion extending from the attachment portion and supporting the handle in a reciprocable manner,
      a diaphragm mounting portion above which the diaphragm is mounted; and
      a receiving portion provided in a position downwardly away from the diaphragm mounting portion,
   the attachment portion is installed in a sandwiched position between the diaphragm mounting portion and the receiving portion,
   the main body has a guide portion provided between the diaphragm mounting portion and the receiving portion,
   the attachment portion has a rotation stabilizing portion installed in a sandwiched position between the diaphragm mounting portion and the guide portion, and
   the rotation stabilizing portion is a guide projection that protrudes toward an internal space of the attachment portion.

2. The manual breast pump according to claim 1, wherein
   the main body has a rotation angle regulating portion that regulates a range of rotation angle of the holding member when the holding member rotates with respect to the main body, and
   a rotation of the attachment portion is restricted by the guide projection coming into abutment with the rotation angle regulating portion.

* * * * *